US008647702B2

(12) United States Patent
Shen et al.

(10) Patent No.: US 8,647,702 B2
(45) Date of Patent: Feb. 11, 2014

(54) MAINTAINING A FIXED DISTANCE BY PROVIDING AN AIR CUSHION DURING COATING OF A MEDICAL DEVICE

(75) Inventors: Randy Shen, Sunnyvale, CA (US); Michael J. Leonard, Palo Alto, CA (US); Anthony S. Andreacchi, San Jose, CA (US)

(73) Assignee: Abbott Laboratories, Santa Clara, CA (US)

( * ) Notice: Subject to any disclaimer, the term of this patent is extended or adjusted under 35 U.S.C. 154(b) by 91 days.

(21) Appl. No.: 13/158,101

(22) Filed: Jun. 10, 2011

(65) Prior Publication Data

US 2012/0315375 A1     Dec. 13, 2012

(51) Int. Cl.
*A61M 25/00* (2006.01)

(52) U.S. Cl.
USPC ............ 427/2.28; 427/2.1; 118/305; 118/320

(58) Field of Classification Search
USPC ........................... 427/2.1, 2.28; 118/305, 320
See application file for complete search history.

(56) References Cited

U.S. PATENT DOCUMENTS

| | | | |
|---|---|---|---|
| 4,748,982 A | 6/1988 | Horzewski et al. |
| 5,300,085 A | 4/1994 | Yock |
| 5,370,614 A | 12/1994 | Amundson et al. |
| 5,464,650 A | 11/1995 | Berg et al. |
| 5,496,346 A | 3/1996 | Horzewski et al. |
| 5,591,227 A | 1/1997 | Dinh et al. |
| 5,626,600 A | 5/1997 | Horzewski et al. |
| 5,649,977 A | 7/1997 | Campbell |
| 5,911,452 A | 6/1999 | Yan |
| 5,980,972 A | 11/1999 | Ding |
| 6,120,847 A | 9/2000 | Yang et al. |
| 6,406,457 B1 | 6/2002 | Wang et al. |
| 6,478,807 B1 | 11/2002 | Foreman et al. |
| 6,494,906 B1 | 12/2002 | Owens |
| 6,669,980 B2 | 12/2003 | Hansen |
| 6,676,987 B2 | 1/2004 | Zhong et al. |
| 6,743,462 B1 | 6/2004 | Pacetti |
| 7,241,344 B2 | 7/2007 | Worsham et al. |
| 7,335,227 B2 | 2/2008 | Jalisi |
| 7,378,105 B2 | 5/2008 | Burke et al. |
| 7,445,792 B2 | 11/2008 | Toner et al. |
| 7,455,876 B2 | 11/2008 | Castro et al. |
| 7,504,125 B1 | 3/2009 | Pacetti et al. |
| 7,524,527 B2 | 4/2009 | Stenzel |

(Continued)

OTHER PUBLICATIONS

U.S. Appl. No. 12/882,953, filed Jan. 15, 2013 Non-Final Office Action.

(Continued)

*Primary Examiner* — Dah-Wei Yuan
*Assistant Examiner* — Andrew Bowman
(74) *Attorney, Agent, or Firm* — Randy Shen, Esq.; Baker Botts LLP

(57) ABSTRACT

System and method for coating an expandable member of a medical device comprising a support structure to support the expandable member and an applicator positioned with at least one outlet proximate a surface of an expandable member. A drive assembly establishes relative movement between the at least one outlet and the surface of the expandable member to apply fluid on the surface of the expandable member along a coating path. A positioning device maintains a substantially fixed distance between the at least one outlet and the surface of the expandable member during relative movement therebetween by ejecting a pressurized medium against the surface of the expandable member.

18 Claims, 6 Drawing Sheets

(56) References Cited

U.S. PATENT DOCUMENTS

| | | | |
|---|---|---|---|
| 2004/0062875 A1 | 4/2004 | Chappa et al. | |
| 2004/0073284 A1 | 4/2004 | Bates et al. | |
| 2004/0234748 A1 | 11/2004 | Stenzel | |
| 2005/0158449 A1* | 7/2005 | Chappa | 427/2.1 |
| 2005/0196518 A1 | 9/2005 | Stenzel | |
| 2007/0031611 A1 | 2/2007 | Babaev | |
| 2007/0088255 A1 | 4/2007 | Toner et al. | |
| 2007/0179591 A1 | 8/2007 | Baker et al. | |
| 2008/0113081 A1 | 5/2008 | Hossainy et al. | |
| 2009/0226598 A1 | 9/2009 | Feng et al. | |
| 2010/0023108 A1 | 1/2010 | Toner et al. | |
| 2010/0030183 A1 | 2/2010 | Toner et al. | |
| 2010/0055294 A1 | 3/2010 | Wang et al. | |
| 2011/0281019 A1 | 11/2011 | Gong et al. | |
| 2011/0281020 A1 | 11/2011 | Gong et al. | |
| 2012/0022540 A1 | 1/2012 | Chasmawala et al. | |
| 2012/0064223 A1 | 3/2012 | Gamez et al. | |
| 2012/0065583 A1 | 3/2012 | Serna et al. | |
| 2012/0128863 A1 | 5/2012 | Nguyen et al. | |
| 2012/0143054 A1 | 6/2012 | Eaton et al. | |
| 2012/0315374 A1 | 12/2012 | Nguyen et al. | |
| 2012/0315376 A1 | 12/2012 | Nguyen et al. | |

OTHER PUBLICATIONS

U.S. Appl. No. 12/882,990, filed Dec. 6, 2012 Non-Final Office Action.
U.S. Appl. No. 12/882,990, filed Apr. 8, 2013 Response to Non-Final Office Action.
U.S. Appl. No. 13/108,283, filed Mar. 28, 2013 Non-Final Office Action.
U.S. Appl. No. 12/882,953, filed Apr. 12, 2013 Response to Non-Final Office Action.
U.S. Appl. No. 13/280,067, filed Apr. 26, 2013 Applicant Summary of Interview with Examiner.
U.S. Appl. No. 13/109,156, filed Apr. 26, 2013 Restriction Requirement.
U.S. Appl. No. 13/158,057, filed Apr. 26, 2013 Restriction Requirement.
U.S. Appl. No. 12/882,990, filed Sep. 15, 2010.
U.S. Appl. No. 13/158,057, filed Jun. 10, 2011.
U.S. Appl. No. 13/158,131, filed Jun. 10, 2011.
Unverdoben, Martin, "The Paclitaxel-Eluting PTCA-Balloon Catheter in Coronary Artery Disease PEPCAD I-SVD PEPCAD II-ISR",Clinical Research Institute, Center for Cardiovascular Diseases, 2005-2006, Rotenburg/Fulda, Germany.
U.S. Appl. No. 12/882,953, filed Sep. 15, 2010.
U.S. Appl. No. 13/280,067, filed Oct. 24, 2011.
U.S. Appl. No. 13/109,156, filed Sep. 10, 2013 Non-Final Office Action.
U.S. Appl. No. 12/882,953, filed Aug. 16, 2013 Final Office Action.
U.S. Appl. No. 13/158,057, filed Sep. 12, 2013 Non-Final Office Action.
U.S. Appl. No. 12/882,990, filed Aug. 1, 2013 Final Office Action.
PlumbingSupply.com, "Pipe Hangers and Brackets", (Feb. 2001), www.plumbingsupply.com/pipehangers.htlm.
Vivekanandhan, et al., "Computer-Aided Torch Trajectory Generation for Automated Coating of Parts with Complex Surfaces", *Journal of Thermal Spray Technology,* 3(2):208-215 (1994).
Cornell, Maintaining Distance Using Sonar video, Youtube (2010) http://www.youtube.com/watch?v=Pj6Jxo2Sqgw, [Downloaded on Sep. 16, 2013].

* cited by examiner

MAINTAINING A FIXED DISTANCE BY PROVIDING AN AIR CUSHION DURING COATING OF A MEDICAL DEVICE

BACKGROUND OF THE DISCLOSED SUBJECT MATTER

1. Field of the Disclosed Subject Matter

The presently disclosed subject matter is related to the delivery of a therapeutic agent from an interventional medical device. Particularly, the disclosed subject matter relates to the method and system for maintaining a fixed distance between an outlet of an applicator and the surface of an expandable member during application of one or more therapeutic agents.

2. Description of Related Subject Matter

Atherosclerosis is a syndrome affecting arterial blood vessels. It is characterized by a chronic inflammatory response in the walls of arteries, which is in large part due to the accumulation of lipid, macrophages, foam cells and the formation of plaque in the arterial wall. Atherosclerosis is commonly referred to as hardening of the arteries, although the pathophysiology of the disease manifests itself with several different types lesions ranging from fibrotic to lipid laden to calcific. Angioplasty is a vascular interventional technique involving mechanically widening an obstructed blood vessel, typically caused by atherosclerosis.

During angioplasty, a catheter having a folded balloon is inserted into the vasculature of the patient and is passed to the narrowed location of the blood vessel at which point the balloon is inflated to the desired size by fluid pressure. Percutaneous coronary intervention (PCI), commonly known as coronary angioplasty, is a therapeutic procedure to treat the stenotic regions in the coronary arteries of the heart, often found in coronary heart disease. In contrast, peripheral angioplasty, commonly known as percutaneous transluminal angioplasty (PTA), generally refers to the use of mechanical widening of blood vessels other than the coronary arteries. PTA is most commonly used to treat narrowing of the leg arteries, especially, the iliac, external iliac, superficial femoral and popliteal arteries. PTA can also treat narrowing of carotid and renal arteries, veins, and other blood vessels.

Although the blood vessel is often successfully widened by angioplasty, sometimes the treated region of the blood vessel undergoes vasospasm, or abrupt closure after balloon inflation or dilatation, causing the blood vessel to collapse after the balloon is deflated or shortly thereafter. One solution to such collapse is stenting the blood vessel to prevent collapse. A stent is a device, typically a metal tube or scaffold that is inserted into the blood vessel after, or concurrently with angioplasty, to hold the blood vessel open.

While the advent of stents eliminated many of the complications of abrupt vessel closure after angioplasty procedures, within about six months of stenting a re-narrowing of the blood vessel can form, a condition known as restenosis. Restenosis was discovered to be a response to the injury of the angioplasty procedure and is characterized by a growth of smooth muscle cells and extracellular matrix—analogous to a scar forming over an injury. To address this condition, drug eluting stents were developed to reduce the reoccurrence of blood vessel narrowing after stent implantation. A drug eluting stent is a stent that has been coated with a drug, often in a polymeric carrier, that is known to interfere with the process of re-narrowing of the blood vessel (restenosis). Examples of various known drug eluting stents are disclosed in U.S. Pat. Nos. 5,649,977; 5,464,650; 5,591,227; 7,378,105; 7,445,792; 7,335,227, each of which are hereby incorporated by reference in their entirety. However, a drawback of drug eluting stents is a condition known as late stent thrombosis. This is an event where a blood clot forms inside the stent, which can occlude blood flow.

Drug coated balloons are believed to be a viable alternative to drug eluting stents in the treatment of atherosclerotic lesions. In a study which evaluated restenosis, and the rate of major adverse cardiac events such as heart attack, bypass, repeat stenosis, or death in patients treated with drug coated balloons and drug eluting stents, the patients treated with drug coated balloons experienced only 3.7% restenosis and 4.8% MACE (material adverse coronary events) as compared to patients treated with drug eluting stents, in which restenosis was 20.8 percent and 22.0 percent MACE rate. (See, PEP-CAD II study, Rotenburg, Germany)

However, drug coated balloons present certain unique challenges. For example, the drug carried by the balloon needs to remain on the balloon during delivery to the lesion site, and released from the balloon surface to the blood vessel wall when the balloon is expanded inside the blood vessel. For coronary procedures, the balloon is typically inflated for less than one minute, typically about thirty seconds. The balloon inflation time may be longer for a peripheral procedure, however typically even for peripheral procedures the balloon is expanded for less than 5 minutes. Due to the short duration of contact between the drug coated balloon surface and the blood vessel wall, the balloon coating must exhibit efficient therapeutic agent transfer and/or efficient drug release during inflation. Thus, there are challenges specific to drug delivery via a drug coated or drug eluting balloon that are not present with a drug eluting stent.

Furthermore, conventional techniques for applying a coating, such as a therapeutic agent, may not be desirable for coating balloons, or other expandable members of medical devices. Such conventional techniques include spraying (air-atomization, ultrasonic, electrostatic, etc.), dip-coating, spin-coating, vapor deposition, roll coating, micro-droplet coating, etc. However, it is desirable to control the amount or dosage of therapeutic agent applied to the surface of the expandable member, and the location in which the therapeutic agent is applied. Many conventional techniques do not provide sufficient control over dosage, coating uniformity or edge control. Such control is further compromised when coating a medical device having a non-uniform configuration, such as a tapered balloon or a partially-inflated balloon, or when coating a medical device having a non-symmetrical surface, such as a balloon having a warped or bowed configuration. For example, peripheral balloons, being longer than coronary balloons, are more susceptible to warping or bowing along the longitudinal axis when inflated. Consequently, the amount and uniformity of coating applied to the balloon surface using conventional techniques may be compromised due to the non-uniform shape of the expandable member.

Thus there remains a need for, and an aim of the disclosed subject matter is directed toward, maintaining a fixed distance between the coating applicator and the surface of the expandable member during the application of one or more therapeutic agents thereto.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a system and method of coating an expandable member of a medical device. The method of coating an expandable member of a medical device comprises providing an applicator in fluid communication with a fluid source, with the applicator having at least one outlet for applying fluid therefrom, and positioning the applicator proximate a surface of an expandable member. Relative movement is established between the at least one outlet and the surface of the expandable member along a coating path while maintaining a substantially fixed distance between the at least one outlet and the surface of the expandable member during relative movement therebetween. A pressurized medium is ejected to maintain a substantially fixed distance between the at least one outlet and the surface of the expandable member during relative movement therebetween. Fluid is applied from the at least one outlet to form a coating of fluid on the surface of the expandable member along the coating path.

The disclosed subject matter also provides a system for coating an expandable member of a medical device. The system includes a support structure to support an expandable member of a medical device; and an applicator in fluid communication with a fluid source. The applicator has at least one outlet for applying fluid of the fluid source therefrom, and is positioned with the t least one outlet proximate a surface of an expandable member supported by the support structure. The system includes a drive assembly to establish relative movement between the at least one outlet and the surface of the expandable member to apply fluid on the surface of the expandable member along a coating path, and a positioning device ejecting a pressurized medium to maintain a substantially fixed distance between the at least one outlet and the surface of the expandable member during relative movement therebetween.

The substantially fixed distance between the expandable member and the at least one outlet is maintained by ejecting a pressurized medium against the surface of the expandable member. Particularly, the pressurized medium is ejected from a positioning device to create a lifting force capable of displacing the at least one outlet so as to track the surface of the expandable member. For example, the at least one outlet is joined to the positioning device, which is operatively coupled to a guide. A change in pressure of the pressurized medium, e.g., air, displaces the positioning device relative to the guide. The at least one outlet can be disposed adjacent the positioning device, or within the positioning device. Further, the positioning device can include a plurality of hinges and be configured for lateral and vertical displacement. In one embodiment, the position device can include a sensor to measure the pressure of the pressurized medium. In one embodiment, the substantially fixed distance is less than about 40 times a dimension of the outlet.

It is to be understood that both the foregoing general description and the following detailed description are examples and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

DETAILED DESCRIPTION

Reference will now be made in detail to embodiments of the disclosed subject matter, an example of which is illustrated in the accompanying drawing. The method and corresponding steps of the disclosed subject matter will be described in conjunction with the detailed description of the system.

The methods and systems presented herein can be used for applying one or more coatings to a medical device. The disclosed subject matter is particularly suited for applying a uniform coating of therapeutic agents, and other fluid compounds, to select portions of an expandable member. While the disclosed subject matter references application of a fluid to an expandable member, it is to be understood that the methods and systems disclosed herein can also be employed to apply therapeutic, polymeric, or matrix coatings to various surfaces of medical devices, as so desired.

The disclosed subject matter provides a method, and corresponding system, to coat an expandable member, or select portions thereof, by a variety of application processes while maintaining a substantially fixed distance between the outlet of the applicator and the surface of the expandable member.

In accordance with the disclosed subject matter, a system and corresponding method of coating an expandable member of a medical device comprises providing an applicator in fluid communication with a fluid source, with the applicator having at least one outlet for applying fluid therefrom, and positioning the applicator proximate a surface of an expandable member. Relative movement is established between the at least one outlet and the surface of the expandable member along a coating path while maintaining a substantially fixed distance between the at least one outlet and the surface of the expandable member during relative movement therebetween, wherein maintaining the substantially fixed distance includes displacing the at least one outlet to track the surface of the expandable member. From the fixed distance, fluid is applied from the at least one outlet to form a coating of fluid on the surface of the expandable member along the coating path.

Figure 1:
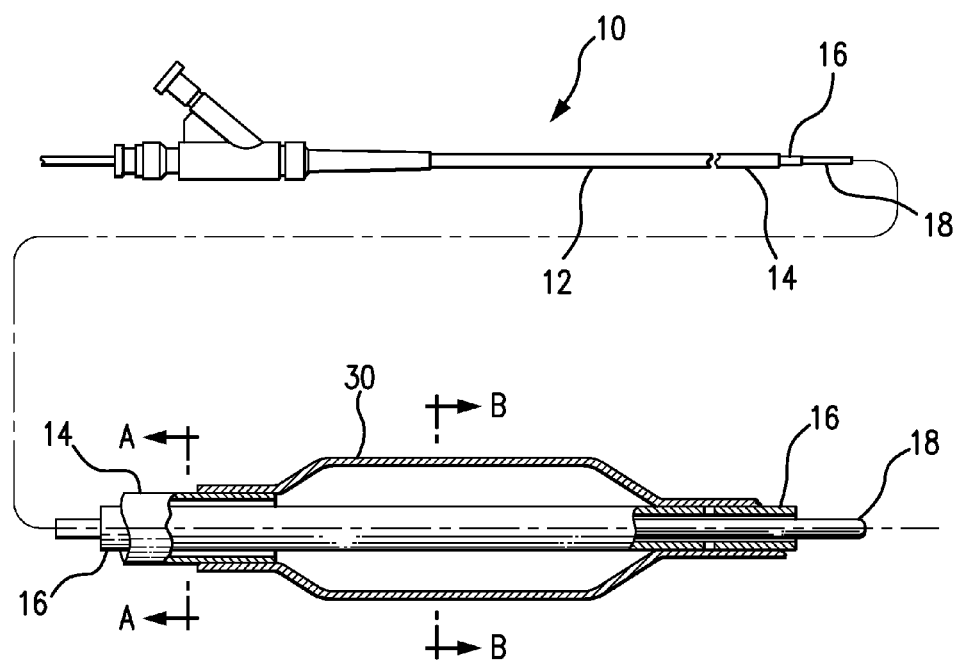
FIG. 1 is a schematic side view in partial cross-section of a representative balloon catheter in accordance with the disclosed subject matter.
Figures 1A, 1B:
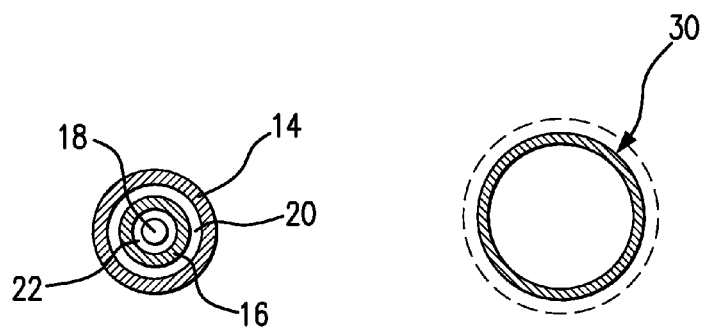
FIG. 1A is a cross-sectional view taken along lines A-A in FIG. 1.
FIG. 1B is a cross-sectional view taken along lines B-B in FIG. 1.

For purpose of explanation and illustration, and not limitation, an embodiment of a medical device having an expandable member is shown schematically in FIGS. 1 and 1A. Particularly, and as illustrated, the medical device embodied herein is a balloon catheter 10, which includes an elongated catheter shaft 12 having a proximal end and having a distal end and an expandable member 30 located proximate the distal end of the catheter shaft. The expandable member, or balloon as depicted herein for purpose of illustration and not limitation, has an outer surface and an inner surface disposed at the distal end portion of the catheter shaft. In accordance with the disclosed subject matter, a coating is applied to at least a portion of the outer surface of the balloon.

The elongated catheter shaft 12 comprises an outer tubular member 14 and an inner tubular member 16. The outer tubular member 14 defines an inflation lumen 20 disposed between the proximal end portion and the distal end portion of the catheter shaft 12. Specifically, as illustrated in FIG. 1A, the coaxial relationship of this representative embodiment defines an annular inflation lumen 20 between the inner tubular member 16 and the outer tubular member 14. The expandable member 30 is in fluid communication with the inflation lumen 20. The inflation lumen can supply an inflation medium under positive pressure and can withdraw the inflation medium, i.e. provide negative pressure, from the expandable member. The expandable member 30 can thus be inflated and deflated. The elongated catheter is sized and configured for delivery through a tortuous anatomy, and can further include a guidewire lumen 22 that permits it to be delivered over a guidewire 18. As illustrated in FIG. 1A, the inner tubular member 16 defines the guidewire lumen 22 for the guidewire 18. Although FIGS. 1 and 1*b* illustrate the guidewire lumen formed as a separate inner member having an over-the-wire (OTW) construction, the guidewire lumen can be formed of a dual lumen member with either an over-the-wire (OTW) or a rapid-exchange (RX) construction, as is well known in the art.

A wide variety of balloon catheters and expandable members constructions are known and suitable for use in accordance with the disclosed subject matter. For example, the expandable member can be made from polymeric material such as compliant, non-compliant or semi-compliant polymeric material or polymeric blends. Examples of such suitable materials include, but are not limited to, nylon 12, nylon 11, nylon 9, nylon 6, nylon 6/12, nylon 6/11, nylon 6/9, and nylon 6/6, polyurethane, silicone-polyurethane, polyesters, polyester copolymers, and polyethylene. Examples of other balloon and catheter embodiments which can be employed in accordance with the disclosed subject matter include U.S. Pat. Nos. 4,748,982; 5,496,346; 5,626,600; 5,300,085; and 6,406,457 and U.S. patent application Ser. Nos. 12/371,426; 11/539,944; and 12/371,422, each of which is hereby incorporated by reference in its entirety.

In one embodiment, the coating is applied to the expandable member of the fully assembled medical device. As described above with reference to FIGS. 1A-B, medical devices such as the catheter 10 include a plurality of components which are typically manufactured as separate discrete components and thereafter assembled together. Applying a coating to the expandable member at an upstream stage of an assembly line can require extensive measures to minimize or prevent the coating from being exposed to various equipment and processes during the downstream stages of the assembly line. Such exposure can render the coating prone to damage and/or contamination during final assembly of the catheter, and can result in scrapping of the entire catheter. Similarly, coating of the expandable member prior to assembly of the catheter can result in contamination of equipment in the assembly line if appropriate measures are not taken. In order to avoid such damage and exposure in conventional catheter assembly lines, additional equipment including monitoring and safety controls would be required. Accordingly, applying the coating to the expandable member after assembly of the catheter, as disclosed herein, avoids the unnecessary complexity and excessive costs associated with a modified assembly line.

In accordance with the disclosed subject matter, any of a variety of fluid compositions can be applied to the expandable member. For example, the fluid can include a therapeutic agent for treatment of a disease state. Examples of suitable therapeutic agents include anti-proliferative, anti-inflammatory, antineoplastic, antiplatelet, anti-coagulant, anti-fibrin, antithrombotic, antimitotic, antibiotic, antiallergic and antioxidant compounds. Such therapeutic agents can be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, and a retroviral vector. As embodied herein, and for purpose of illustration, the therapeutic agents include a cytostatic drug. The term "cytostatic" as used herein means a drug that mitigates cell proliferation but allows cell migration. These cytostatic drugs include for the purpose of illustration and without limitation, macrolide antibiotics, rapamycin, everolimus, zotarolimus, biolimus, temsirolimus, deforolimus, novolimus, myolimus, structural derivatives and functional analogues of rapamycin, structural derivatives and functional analogues of everolimus, structural derivatives and functional analogues of zotarolimus and any marcrolide immunosuppressive drugs. The term "cytotoxic" as used herein means a drug used to inhibit cell growth, such as chemotherapeutic drugs. Some non-limiting examples of cytotoxic drugs include vincristine, actinomycin, cisplatin, taxanes, paclitaxel, and protaxel.

Additionally or alternatively, the fluid can include other compounds or additives, such as polymers, binding agents, plasticizers, solvents, surfactants, additives, chelators, fillers, and the like. A formulation of the disclosed subject matter can include zotarolimus, polyvinylpyrrolidone and glycerol. In one embodiment the therapeutic agent can be provided in liquid form or dissolved in a suitable solvent. In another embodiment, the therapeutic agent is provided as a particulate and mixed in a suitable carrier for application as a fluid.

In accordance with an aspect of the disclosed subject matter, a variety of techniques for applying a coating of therapeutic agent can be employed, such as spraying (air-atomization, ultrasonic, electrostatic, etc.), vapor deposition, microdroplet coating, etc. Additionally or alternatively, a direct coating process can be used and is embodied herein, as further disclosed in U.S. Pat. No. 7,455,876 and U.S. Patent Publication No. 2010/0055294, the entirety of each is hereby incorporated by reference, can be employed in accordance with the disclosed subject matter. For purpose of illustration and not limitation, reference will be made to a direct coating process, although the disclosed subject matter is equally applicable to other suitable coating application techniques.

Figure 2:
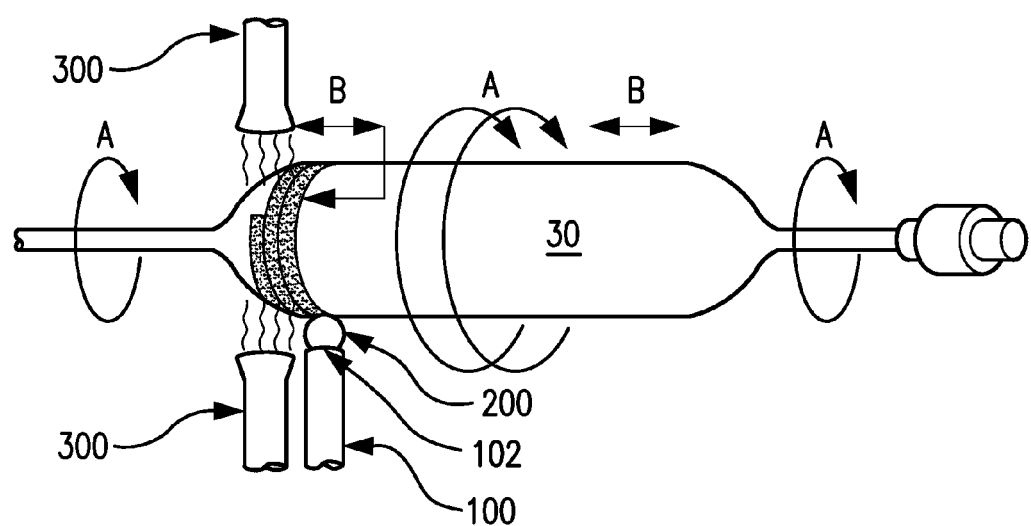
FIG. 2 is a schematic view of an applicator assembly for direct fluid coating on the surface of an expandable member.

An embodiment of the direct coating process and system is illustrated in FIG. 2 for purpose of explanation and not limitation. The applicator depicted herein is shown as a pipette 100 having an outlet positioned proximate expandable member 30 such that the fluid applied by the pipette is deposited on the surface of the expandable member 30. As the coating solution is delivered from a fluid source, e.g. reservoir (not shown), through the dispenser outlet, a continuous fluid medium or bead 200 of solution directly contacts the surface of the expandable member. FIG. 2 depicts the pipette 100 generally normal or at a right angle to the balloon surface. However, alternative alignments and orientations can be used as desired or needed for the type and dimensions of expandable members.

A positive pressure is applied to assist with dispensing fluid from the outlet. In addition, due to capillary action, the surface tension pulls the bead of coating solution 200 onto the surface of the expandable member. Furthermore, the outlet can be heated prior to and/or during the dispensing of the coating solution. The heating of the dispenser can reduce the viscosity of the coating solution and therefore accelerate the coating process as well as reduce the potential for clogging or occluding of the dispenser outlet 102. FIG. 2 depicts the outlet generally at a right angle to the balloon surface.

Coating process and systems of the disclosed subject matter can be performed with the expandable member in a partially or fully inflated condition, or in a deflated condition if desired. If deflated, the expandable member can have a generally smooth exposed surface if made of a compliant material, or can be pleated, folded, wrinkled or pressed if made of a semi-compliant or non-compliant material. For purpose of illustration, FIG. 2 shows the expandable member 30 in an inflated condition to allow coating of all or select portions of the outer surface. Additionally, the temperature of the expansion medium, or the expandable member itself, can be controlled to further maintain or define the contour of the expandable member.

As fluid is delivered from the applicator 100, relative movement is established between the applicator 100 and the expandable member 30 to effect a continuous or patterned coating path as desired. For example, and as depicted in FIG. 2, the coating path can define a generally continuous spiral or helical pattern along the outer surface of the expandable member. Alternatively, coating paths can be established as discrete circumferential rings, discrete lines extending along the expandable members longitudinal axis, or combinations or portions thereof.

The relative movement can include rotation, translation, or combinations thereof, of either, or both, the expandable member and the applicator. For example, the expandable member 30 can be rotated about its central axis, as shown by arrows A in FIG. 2, and simultaneously translated along the central axis, as shown by arrow B in FIG. 2. Additionally, or alternatively the expandable member 30 can rotate relative a first axis, and the applicator 100 translate relative the axis, e.g., to define a helical coating path. Accordingly, any number of coating paths can be selected and provided on the expandable member. The various movements described herein can be performed simultaneously, sequentially, continuously or intermittently, as so desired. As embodied herein, the expandable member can be rotated at a speed of between about 5 and 1000 rpm, depending upon the coating fluid and related parameters during coating, and translated relative to the applicator at a speed of between about 0.02 and 10 cm/sec.

The desired portions or areas of the expandable member can be coated with a single pass or cycle of relative movement between the expandable member and applicator. Alternatively, a plurality of passes or cycles of coating operation can be performed. Such multiple passes or cycles allow for further variation in the coating properties along the expandable member length or select areas. For example, one portion of the expandable member can be coated with a different number of coating layers of fluid than another portion of the expandable member thereby creating a gradient of the coating on the expandable member. Further, various layers of different coating formulations can be applied to the expandable member using the method and system disclosed herein. For example, one or more layers of therapeutic-free primers, concentrated therapeutic layers, drug-excipient layers, and/or release control layers can be applied. These varied coating properties allow for greater flexibility and customization of the catheter to provide a greater range of applications and uses.

In accordance with another aspect of the disclosed subject matter, drying can be employed to accelerate the coating process, such as by applying heat, forced gas, cooled gas, vacuum, infra-red energy, microwave energy, or a combination thereof to the coated surface of the expandable member. With regard to a direct coating operation, for purpose of illustration and not limitation, FIG. 2 shows a dryer 300 can be provided upstream of or adjacent to the applicator for drying concurrent with or shortly after coating application. In one embodiment, the drying nozzle can be collinear with the applicator by circumscribing or surrounding the applicator with an annular opening. Additionally or alternatively, drying can be conducted between successive coating passes or cycles. The dryer 300 can be oriented at any suitable angle relative to the surface of the expandable member, and can be configured for relative movement with or independent of the applicator relative to the expandable member.

While the direct coating applicator of the embodiment illustrated in FIG. 2 is depicted as a pipette, additional or alternative applicators can be employed. Some examples of suitable direct coating applicators include flexible tubing, coaxial tubing, hypotubes, dies, ball-bearing dispense tubing, syringe, needles, brushes, sponges, cones and foam applicators. Furthermore, FIG. 2 depicts a direct coating applicator having a single outlet 102, a plurality of outlets can be employed if desired. The outlets can be disposed adjacent each other along the axis of the expandable member, and/or spaced circumferentially about the expandable member. In this regard, one or more of a plurality of reservoirs containing the same or different coating solutions can be provided in fluid communication with each outlet of the applicator, respectively. As with the outlet 102 of FIG. 2, each outlet 102 of the applicator can be positioned at various locations and orientations relative to the surface of the expandable member. Additionally, the expandable member 30 can be oriented in a generally horizontal position, as shown in FIG. 2, vertically, or at or at any angle between as suitable. For example, arranging the expandable member in a vertical configuration can be advantageous for larger size expandable members, e.g., peripheral balloons, to allow gravitational force to act parallel with the longitudinal axis of the expandable member to reduce deformation of the expandable member and associated catheter shaft.

In accordance with another aspect of the disclosed subject matter, the tracking mechanism can be configured for displacement of the applicator outlet in at least one direction in a plane generally orthogonal to the longitudinal axis in which the expandable member is supported. This aspect is particularly beneficial for use with an expandable member having a distorted or asymmetric configuration along its longitudinal axis, such as a bowed or warped balloon. For example, an expandable member of significant length, such as a peripheral balloon, can tend to bow or warp and thus result in an asymmetric shape. Likewise, distorted configurations can result from the particular material properties used for the expandable member, as well as the various manufacturing processes performed e.g., blowing, stretching, shrinking, welding, etc.

Figure 3A:
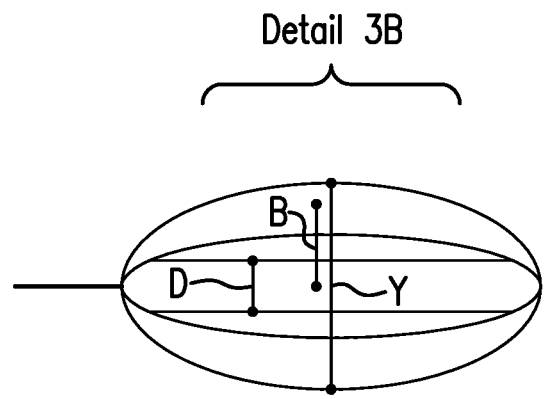
FIGS. 3A and 3B are a schematic representation and an enlarged detail section, respectively, of an expandable member having a bowed configuration relative to a true symmetrical expandable member along a common longitudinal axis.
Figure 3B:
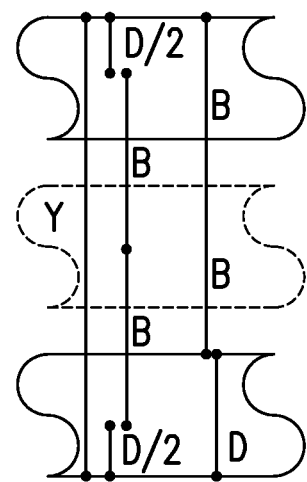

For purpose of explanation, one example of a quantitative measurement of the amount of asymmetry of an expandable member is depicted in FIGS. 3A and 3B. Particularly, FIG. 3A schematically depicts the distortion of a bowed balloon during rotation relative to a true symmetrical expandable member. FIG. 3B is an enlarged detail view of the schematic depiction of FIG. 3A to demonstrate certain relevant dimensions. As depicted, the amount of bowing of the expandable member is defined by the formula B=(Y−D)/2, wherein B is defined as the amount of bowing from a true longitudinal axis; D is defined as the diameter of the expandable member; and Y is defined as the distance from a surface of the expandable member with respect to the true longitudinal axis. Accordingly, for an expandable member, which is symmetrical about a central axis, the value of B is equal to zero.

Figure 4A:
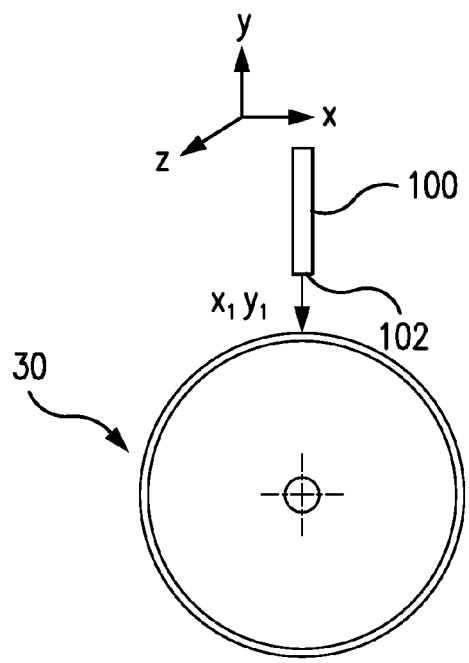
FIGS. 4A and 4B are schematic cross-sectional views of the spaced relationship between an applicator and an expandable member without and with a bowed configuration, respectively.
Figure 4B:
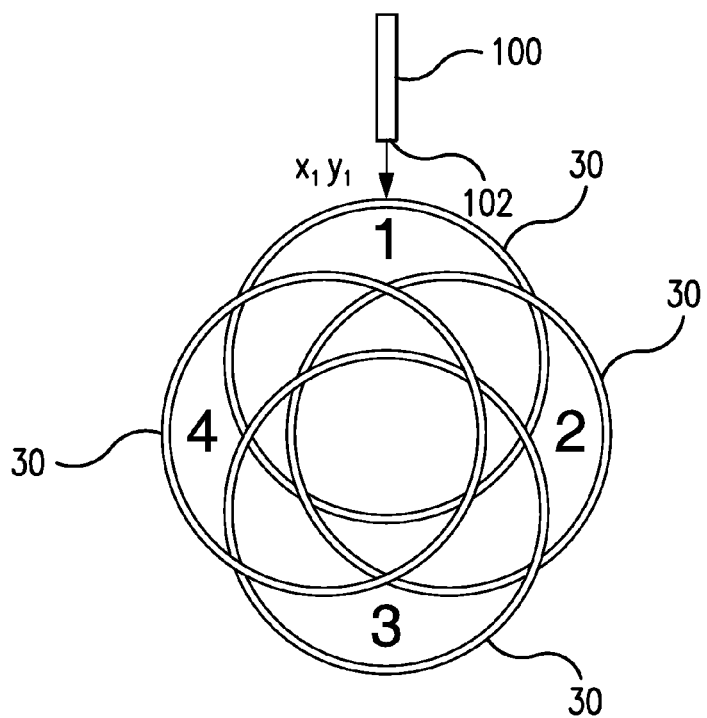

FIG. 4A illustrates a cross-sectional view of a true symmetrical expandable member. As shown in FIG. 4A, as the expandable member is rotated about its central axis, the distance from the applicator outlet to the top center of the balloon remains fixed at a constant position, indicated by coordinates $X_1Y_1$. Accordingly, the applicator outlet can remain in a single and fixed position with the distance between the applicator and the expandable member remaining constant. By contrast, FIG. 4B depicts four (1-4) positions of rotation of an asymmetrical expandable member relative to an applicator outlet maintained in a fixed position. When the asymmetrical expandable member is rotated about its central axis, as illustrated in FIG. 4B, the distance between the fixed applicator outlet and the top center of the rotating expandable member (i.e., $X_1Y_1$ in position 1) will vary in both the X axis and the Y axis—and thus result in a non-uniform coating. For purpose of illustration, the amount of bowing is exaggerated to demonstrate the amount of potential offset from the outlet of an applicator maintained at a fixed location.

Movement of the medical device and/or the outlet of the applicator is accomplished by providing a support assembly or a support structure. The support assembly or support structure can maintain the position of one element, e.g., the applicator, while allowing movement of the other element, e.g., the medical device. Alternatively, the support assembly or support structure can allow movement of both elements. Movement can be performed manually, or by providing a drive assembly with suitable drive source, such as a motor or the like, and appropriate controller as know in the art.

In accordance with the disclosed subject matter, the applicator is maintained at a predetermined or fixed distance from the expandable member surface. Maintaining a fixed distance between the outlet of the applicator and the expandable member, in combination with rotation and translation as discussed above, provides greater control over the coating pattern to be applied to the expandable member surface. Such control provides a consistent and uniform dosage of the therapeutic agent along the surface of the expandable member, resulting in a coating with increased efficacy and good content uniformity. Additionally, maintaining a fixed distance allows greater control for coating an expandable member at discrete locations, if desired, or with non-uniform patterns, such as to create varied local areal density along selected portions of the expandable member.

Furthermore, maintaining a fixed distance between the outlet of the applicator and the expandable member surface reduces the amount of waste or excess coating which is not retained on the expandable member. For example, with spray coating techniques, the amount of waste or excess coating generally increases with the distance between the outlet(s) and the surface of the expandable member. Conversely, if the distance between the outlet of the applicator and the expandable member surface are too small, undesired or accidental contact between the outlet of the applicator and expandable member surface can occur resulting in tearing or scratching of the expandable member surface, abrasion to the coating applied to the expandable member, or bare spots in the coating. The distance between the outlet and the surface of the expandable member can depend upon a number of variables, including viscosity of the fluid, surface tension of the fluid, pump rate of the fluid, diameter of the applicator exit orifice, volatility of the solvents in the fluid, speed at which the fluid is dispensed and/or size of the outlet opening. For example, when using a pipette type applicator for direct coating applications, the distance between the outlet and the surface generally should be less than about 40 times the smallest cross dimension of the outlet.

As disclosed herein, the fixed distance between the at least one outlet of the applicator and the surface of the expandable member is maintained by ejecting a pressurized medium against the surface of the expandable member. The applicator outlet is mounted to be displaceable at least in a direction generally normal to the surface of the expandable member. The pressurized medium thus establishes a substantially constant force to hold or maintain the applicator outlet a substantially constant or fixed distance from the surface of the expandable member. In this manner, the applicator outlet tracks the surface contour of the expandable member during relative movement or translation therebetween. Such a technique is generally suitable for any of a variety of known expandable members, including conventional cylindrical balloons, as well as tapered, shaped and stepped balloons or the like. Also, by tracking the surface of the expandable member, the various coating techniques can adjust for minor distortions or features—whether intentional or unintentional—in the surface of the expandable member. Furthermore, and as described further below, the method and system of the disclosed subject matter also is suitable for use with bowed or warped balloons, such as peripheral balloons that due to their longer lengths can have greater distortions.

Figure 5A:
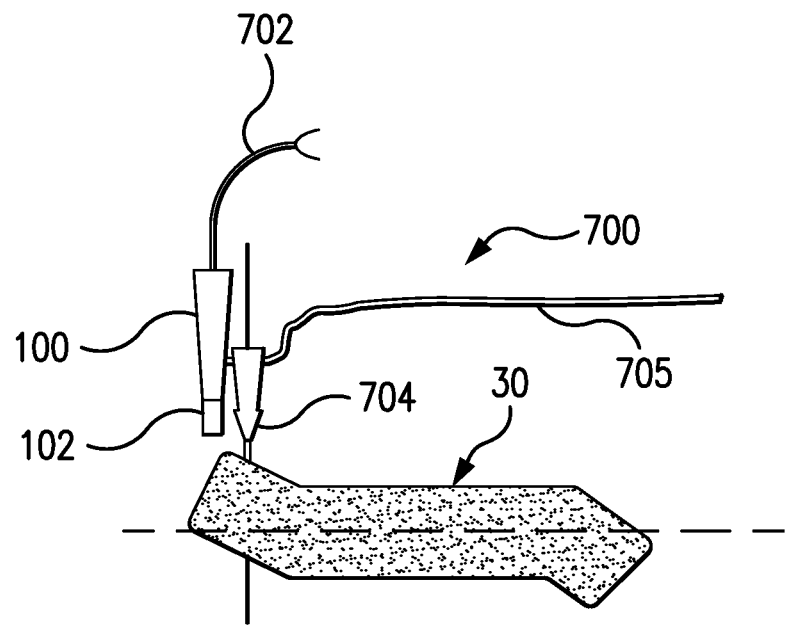
FIGS. 5A and 5B are schematic representations of an expandable member and coating system with a positioning device through various stages of the coating process in accordance with the disclosed subject matter.

In accordance with the disclosed subject matter, the distance between the applicator outlet and the surface of the expandable member can be maintained in a number of ways using a pressurized medium. For example, the fixed distance can be maintained between the applicator outlet and the expandable member surface by employing a positioning device that dispenses a pressurized medium, e.g., a nozzle coupled to a pressurized gas source. In an embodiment of the disclosed subject matter, as illustrated in FIG. 5A, a positioning device 700 is provided to displace the outlet 102 of the applicator 100 so as to track the surface of the expandable member 30. The positioning device 700 includes an ejector 704 fluidly coupled to a pressurized medium source 705 to generate a lifting force sufficient to lift and maintain the at least one outlet the desired fixed distance. The ejector 704 embodied herein is a nozzle, although other suitable configurations known in the art also can be used. At least the outlet 102 of the applicator 100 is coupled to the positioning device 700. For example, and as embodied herein, the outlet 102 of the applicator 100 is rigidly attached or affixed to the positioning device 700 for direct correlation in displacement of the positioning device 704 and the applicator outlet 102.

FIG. 5A depicts the ejector 704 of the positioning device 700 and the applicator outlet 102 arranged in parallel and joined by a connector for 1:1 movement of the two components. As embodied herein, the outlet 102 of the applicator 100 is located adjacent to and/or in close proximity with the ejector 704. The ejector 704 and/or the applicator outlet 102 are mounted for displacement along a guide rail 702 in a direction orthogonal to the longitudinal axis of the expandable member 30, such as generally normal to the surface of the expandable member 30. For example, the guide rail 702 is aligned in a plane generally perpendicular to the longitudinal axis of the expandable member 30 and assists in maintaining a spatial relationship of the applicator outlet 102 with respect to the expandable member 30. Guide rail 702 can be maintained at a generally fixed distance relative the expandable member 30, or alternatively, the guide rail itself can be allowed to move along an axis orthogonal to the longitudinal axis of the expandable member 30 to be positioned closer to or further away from the surface of the expandable member 30. The predetermined arrangements of the applicator 100, positioning device 700 and guide rail 702 can be adjusted as so desired to accommodate various shapes and sizes of expandable members, as well as various types or sizes of applicators.

Accordingly, the ejector 704 of the positioning device 700 dispenses a pressurized medium against the surface of the expandable member to generate a lifting force capable of maintaining the applicator outlet 102 a desired distance from the surface of the expandable member 30. By adjusting the pressure or velocity in which the pressurized medium is ejected from the positioning device 700, the distance between the applicator outlet 102 and the surface of the expandable member 30 can be altered and controlled. Furthermore, the positioning device 700 can include sensors, e.g. pressure transducer, thermocouple, etc., to monitor and adjust the parameters of the pressurized medium ejected from the ejector 704 and thus maintain or alter the fixed distance between the outlet and the surface of the expandable member as desired.

Figure 5B:
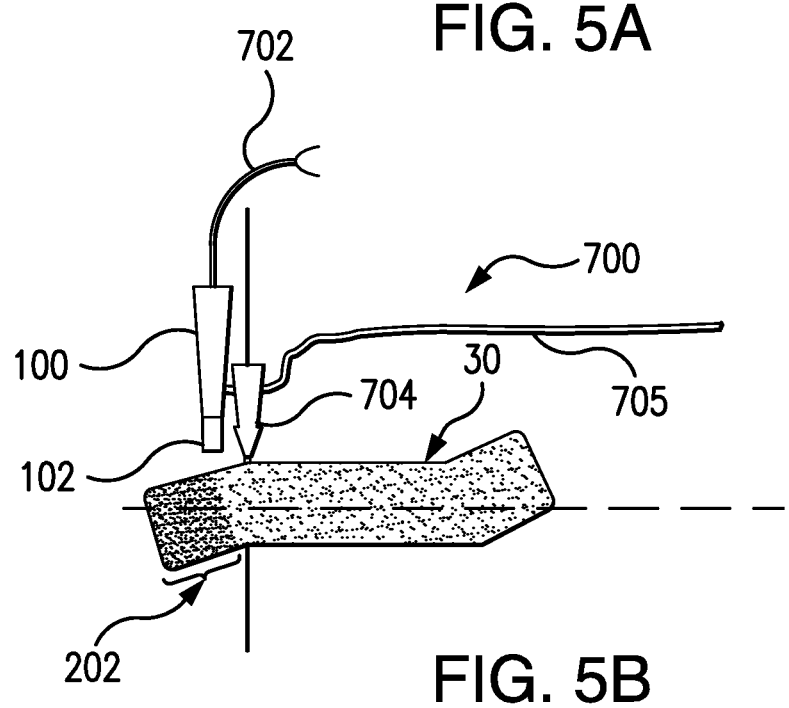

FIGS. 5A-B schematically depict various stages of a coating operation, with various amounts fluid coating 202 applied to the expandable member 30. As variations in the surface of the expandable member 30 are encountered by the positioning device 700, at least the outlet 102 of the applicator 100 is displaced accordingly to maintain a fixed distance between the applicator outlet 102 and the surface of the expandable member 30. In the illustrated embodiment, applicator 100 and positioning device 700 move together relative the expandable member, so as to traverse all or a portion of the length of the expandable member 30 as the expandable member is rotated about its longitudinal axis. The positioning device 700 "floats" or is held in a spaced relationship from the surface of the expandable member by the lifting force of the pressurized medium ejected from the ejector 704. Accordingly, the applicator 100, which is rigidly attached to the positioning device 700, also "floats" along the surface of the expandable member to track the shape and surface contours of the expandable member 30.

As embodied herein, the positioning device 700 is positioned upstream of the outlet 102 of the applicator 100 to avoid contact with newly-applied coating from the outlet 102. For example, the positioning device 700 can be positioned proximal to or laterally adjacent to the outlet 102 such that the positioning device 700 so as not to encounter a fresh or wet coating.

The pressurized medium of the positioning device can be any of a variety of desired gases, including air, oxygen, nitrogen or the like. Additionally, the pressurized medium of the positioning device can include one or more compounds to enhance parameters of the coating process, including purity, uniformity and adhesion. For example, the pressurized medium can be formulated to clean or treat the surface of the expandable member immediately prior to the application of coating fluid. Additionally, or alternatively, the pressurized medium can include a solvent or compound, such as water vapor, to adjust or tune the coating fluid prior to or during the curing process. The pressurized medium also can be heated to assist with drying of as the fluid coating is applied.

Figure 6:
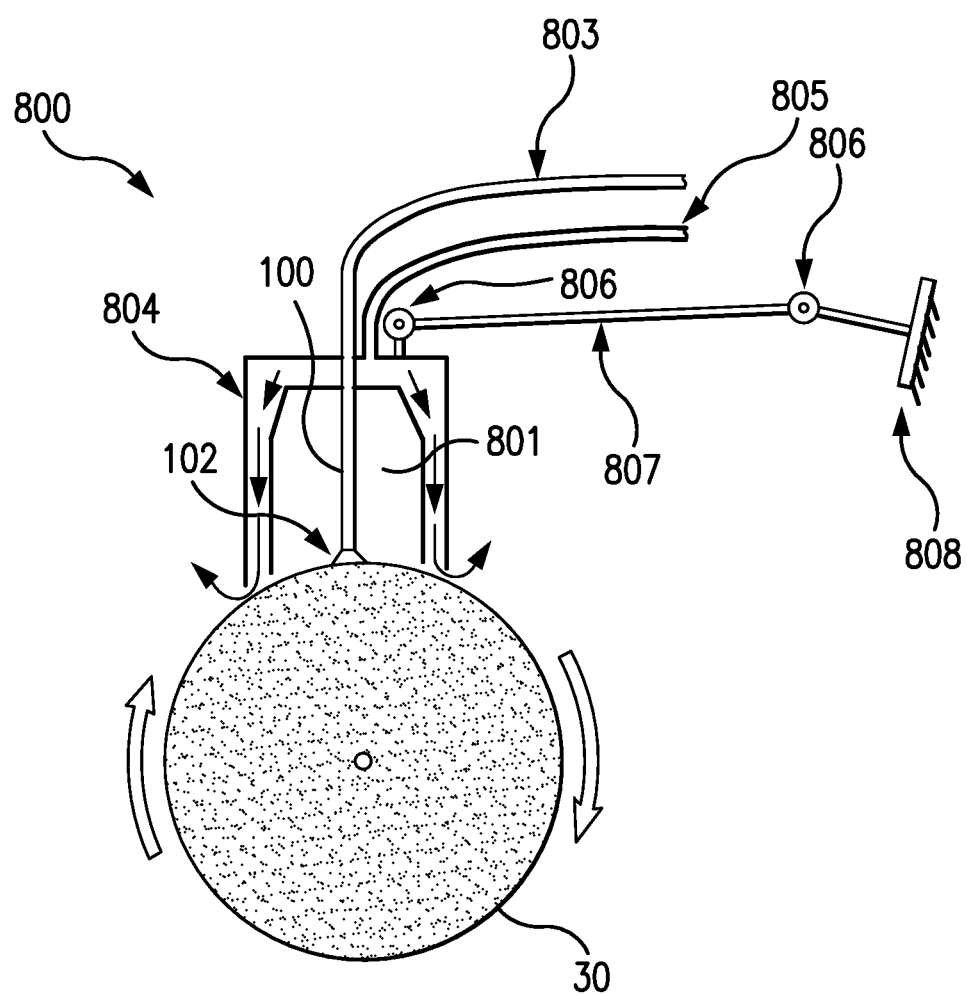
FIG. 6 is a schematic representation of an alternative embodiment of a positioning device in accordance with the disclosed subject matter.

In accordance with another aspect of the disclosed subject matter, the positioning device further defines a chamber for the application of fluid coating by the applicator. For purpose of illustration and not limitation, FIG. 6 schematically shows the positioning device 800 defining a chamber 801 within which the applicator outlet 102 is disposed. The chamber 801 minimizes contamination of the fluid coating being applied by the applicator 700, as well as minimizes loss of the coating fluid and contamination of the surrounding environment such as when a spray applicator or the like is used. Although not shown, the chamber 801 can be vented for removal or recycling of the chamber contents if desired.

An ejector comprising one or more ejecting conduits 804 fluidly-coupled to a pressurized fluid source 805 is disposed along the wall of the chamber 801 to dispense pressurized fluid at sufficient pressure or velocity to maintain the positioning device and thus the applicator outlet 102 a fixed distance from the surface of the expandable member 30. As schematically embodied herein, the ejecting conduit(s) 804 can be defined by and/or between inner and outer walls of the positioning device 800. Alternatively, a plurality of individual conduits 804 can be formed in a spaced relationship along the wall of the chamber 801 to provide a balanced lifting force to float or maintain the desired spaced relationship from the surface of the expandable member 30.

As with the previous embodiment, at least the outlet 102 of the applicator 100 is coupled to the positioning device 800. Particularly, and as embodied herein for purpose of illustration, the outlet 102 of the applicator 100 is secured within the chamber 801 for direct correlation between movement of the positioning device 800 and displacement of the outlet 102. If desired, the relative position of the applicator outlet 102 in the chamber can be adjustable using conventional fasteners or the like. The positioning device 800 of FIG. 6 can be mounted on a guide rail as previously described for movement in a direction orthogonal to the surface of the expandable member. Alternatively, the positioning device 800 can be mounted to allow for two degrees of freedom if desired. For example, and as depicted in FIG. 6 for purpose of illustration and not limitation, the positioning device 800 can include a guide assembly 807 having a plurality of hinges 806. In this manner, the positioning device 800 and thus the applicator outlet 102 can be displaced two directions within a plane orthogonal to the longitudinal axis of the expandable member 30. That is, the balanced lifting force from the conduit(s) 804 will allow the positioning device 800 and thus the applicator outlet 102 to automatically adjust in either or both the X and Y directions as previously defined with reference to FIG. 4A.

As with the previous embodiment, the pressure or velocity in which the pressurized medium is ejected from the positioning device 800 can be adjusted to alter and control the distance between the applicator outlet 102 and the surface of the expandable member 30. Additionally, the positioning device 800 can include sensors, e.g. pressure transducer, thermocouple, etc., to monitor and adjust the parameters of the pressurized medium ejected from the conduit(s) 804. Such sensors can be particularly useful to ensure a balanced lifting force is created by regulating flow through the various ejecting conduits of the positioning device. Likewise, the predetermined arrangements of the applicator 100, positioning device 800 and the guide assembly 807 can be adjusted as so desired to accommodate various shapes and sizes of expandable members, as well as various types or sizes of applicators.

The conduit(s) 804 of the positioning device 800 are generally positioned upstream of the outlet 102 of the applicator 100 or sufficiently downstream to avoid contact with newly-applied coating from the outlet 102. For example, the ejecting conduits 804 can be positioned proximal to the applicator outlet 102 or laterally adjacent to the applicator outlet 102 so as not to encounter a wet coating fluid.

In an embodiment of the system and corresponding method of the disclosed subject matter, the translation of the expandable member with respect to the positioning device is a ratio of 1:1. The expandable member can be inflated to or above nominal pressure to minimize any compressive force resulting from the pressurized fluid impacting the expandable member. By utilizing a positioning device that does not contact the surface of the expandable member, the risk of interfering or disturbing the coating fluid applied by the outlet can be minimized. Additionally, the absence of contact between the expandable member and the positioning device is advantageous in reducing the forces required to establish the relative movement between the expandable member and the outlet of the applicator. As previously noted, the coating method and system of the disclosed subject matter can be performed on a fully assembled medical device, e.g. balloon catheters, wherein the force required to rotate or otherwise move the expandable member is applied to the medical device at a location remote of the expandable member. Therefore, significant force may be required to overcome the friction and inertia of the various components of the medical device in order to achieve movement of the expandable member. Thus, the reduction or minimization of contact with the expandable member is advantageous as the frictional forces generated during the relative movement will in turn be minimized, thereby reducing the amount of force required by the support assembly, or manual operator, to establish relative movement. Furthermore, the various components of a medical device such as a balloon catheter are not torsionally rigid. Therefore undue friction on the expandable member can lead to torsional loading and unloading of the proximal members. This can lead to inconsistent rotation of the medical device, and thus non-uniform coating.

If desired, a protective sheath can be provided to protect the coating during shipping and storage and/or during delivery of the coated expandable member through the body lumen. A variety of sheaths are known, including removable sheaths or balloon covers, retractable sheaths to be withdrawn prior to deployment of the balloon, and elastic sheaths that conform to the balloon upon expansion. Such elastic sheaths can be porous or include apertures along a portion thereof. In operation, the inflation of the expandable member causes the sheath to expand for release of the coating and/or therapeutic agent through the porous wall or apertures to the tissue of the arterial wall. For example, see U.S. Pat. No. 5,370,614 to Amundson, the disclosure of which is incorporated by reference in its entirety.

In accordance with in the disclosed subject matter, an endoprosthesis, e.g., stent, can be mounted on the expandable member. The type of stent that can be used includes, but is not limited to, bare metal stent, drug eluting stent, bioabsorbable stent, balloon-expandable stent, self-expanding stent, pro-healing stent, and self-expanding vulnerable plaque implant. The expandable member can be coated independently of the stent or in conjunction with the stent coating process. The stent coating can contain the same or different therapeutic agents from the catheter or expandable member. However, the particular coating on the catheter or expandable member can have distinct release kinetics from the therapeutic coating on the stent. The coating applied to the expandable member can be allowed to dry prior to placement of the stent thereon.

Alternatively, the endoprosthesis can be positioned and/or crimped on to the expandable member before the coating is allowed to dry or cure past a "tacky" state. This would enable adhesion of the coating between the expandable member and the endoprosthesis. This process increases the retention of the prosthesis onto the expandable member (acting as an endoprosthesis retention enhancer) thus reducing the risk of dislodgement of the endoprosthesis during the torturous delivery through the vascular lumen While the disclosed subject matter is described herein in terms of certain embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A system for coating an expandable member of a medical device, the system comprising:
    a support structure to support an expandable member of a medical device;
    an applicator in fluid communication with a fluid source, the applicator having at least one outlet for applying fluid of the fluid source therefrom, the applicator positioned with the at least one outlet proximate a surface of an expandable member supported by the support structure;
    a drive assembly to establish relative movement between the at least one outlet and the surface of the expandable member to apply fluid on the surface of the expandable member along a coating path; and
    a positioning device to maintain a substantially fixed distance between the at least one outlet and the surface of the expandable member by ejecting a pressurized medium during relative movement therebetween, wherein the positioning device displaces the at least one outlet to track the surface of the expandable member.

2. A system for coating an expandable member of a medical device, the system comprising:

a support structure to support an expandable member of a medical device;

an applicator in fluid communication with a fluid source, the applicator having at least one outlet for applying fluid of the fluid source therefrom, the applicator positioned with the at least one outlet proximate a surface of an expandable member supported by the support structure;

a drive assembly to establish relative movement between the at least one outlet and the surface of the expandable member to apply fluid on the surface of the expandable member along a coating path;

a positioning device to maintain a substantially fixed distance between the at least one outlet and the surface of the expandable member by ejecting a pressurized medium during relative movement therebetween; and a guide operatively coupled to the positioning device, wherein a change in pressure of the pressurized medium displaces the positioning device relative to the guide.

3. The system of claim 1, further comprising a guide operatively coupled to the positioning device, wherein a change in pressure of the pressurized medium displaces the positioning device relative to the guide.

4. The system of claim 3, wherein the at least one outlet is disposed adjacent the positioning device.

5. The system of claim 3, wherein the at least one outlet is disposed within the positioning device.

6. The system of claim 5, wherein the positioning device is configured for lateral and vertical displacement.

7. The system of claim 6, wherein the positioning device is supported by a plurality of hinges for lateral and vertical displacement.

8. The system of claim 1, wherein the positioning device includes a sensor to measure the pressure of the pressurized medium.

9. The system of claim 1, wherein the pressurized medium is air.

10. The system of claim 1, wherein the substantially fixed distance is less than about 40 times a dimension of the outlet.

11. The system of claim 2, wherein the at least one outlet is disposed adjacent the positioning device.

12. The system of claim 2, wherein the at least one outlet is disposed within the positioning device.

13. The system of claim 12, wherein the positioning device is configured for lateral and vertical displacement.

14. The system of claim 13, wherein the positioning device is supported by a plurality of hinges for lateral and vertical displacement.

15. The system of claim 2, wherein the positioning device includes a sensor to measure the pressure of the pressurized medium.

16. The system of claim 2, wherein the pressurized medium is air.

17. The system of claim 2, wherein the substantially fixed distance is less than about 40 times a dimension of the outlet.

18. The system of claim 2, wherein the positioning device displaces the at least one outlet to track the surface of the expandable member.

* * * * *